US00RE37984E

(19) United States
(12) Reissued Patent
Jäckle et al.

(10) Patent Number: US RE37,984 E
(45) Date of Reissued Patent: Feb. 11, 2003

(54) PROCESS FOR ANALYZING LENGTH POLYMORPHISMS IN DNA REGIONS

(75) Inventors: Herbert Jäckle, Göttingen (DE); Diethard Tautz, Köln (DE)

(73) Assignee: Max-Planck-Gesellschaft zur Forderung der Wissenschaften e.V., Gottingen (DE)

(21) Appl. No.: 09/591,383

(22) Filed: Jun. 9, 2000

Related U.S. Patent Documents

Reissue of:
(64) Patent No.: 5,766,847
Issued: Jun. 16, 1998
Appl. No.: 08/145,617
Filed: Nov. 4, 1993

U.S. Applications:
( 63) Continuation of application No. 07/681,494, filed as application No. PCT/EP89/01203 on Oct. 11, 1989, now abandoned.

(30) Foreign Application Priority Data

Oct. 11, 1988 (DE) ..... 38 34 636

(51) Int. Cl.[7] ..... C12P 19/34; C12Q 1/68; C07H 21/04

(52) U.S. Cl. ..... 435/6; 435/194; 435/91.02; 536/23.1; 536/24.3; 536/24.33

(58) Field of Search ..... 435/6, 91.2, 194, 435/810; 536/22.1, 23.1, 24.3, 24.22

(56) References Cited

U.S. PATENT DOCUMENTS

| | | | | |
|---|---|---|---|---|
| 5,075,217 | A | 12/1991 | Weber | 435/6 |
| 5,364,759 | A | 11/1994 | Caskey et al. | 435/6 |

FOREIGN PATENT DOCUMENTS

| | | |
|---|---|---|
| EP | 0 186271 | 10/1985 |
| EP | 0 342717 | 10/1985 |
| EP | 0 200362 | 3/1986 |
| EP | 0 237362 | 3/1986 |
| EP | 0 266787 | 11/1987 |
| WO | 8 907658 | 8/1989 |

OTHER PUBLICATIONS

Nakahori et al., Nucleic Acids Research 14(19):7569–7580, 1988.*
Decorte et al., DNA and Cell Biology 9(6):461–469, 1990.*
Handyside et al., The Lancet 1:347–349, Feb. 18, 1989.*
Ibid., Nature 344:768–770, Apr. 19, 1990.*
Kogan et al., The New England J. Medicine 317(16):985–990, Oct. 15, 1987.*
D. Tautz, DNA Fingerprinting: State of the Science (1993). Edited by S. D. J. Pena et al., Birkhauser Verlag Publishers, Basel. Notes on the definition and nomenclature of tandemly repetitive DNA sequences, pp. 21–29.
E. R. Moxon et al., *Scientific American*, Jan. 1999, pp. 72–77.
D. Tautz, *BioEssays*, vol. 12, No. 1, 1990, pp. 44–46.
W. Xu et al., *Gene*, 204:165–170 (1997).
H. Chen et al., *Human Mutation*, 4:208–211 (1994).
X. Y. Hauge et al., *Human Molecular Genetics*, 2(4):411–415 (1993).
J. M. Hite et al., *Nucleic Acids Research*, 1996, vol. 24, No. 12, pp. 2429–2434.
D. Tautz, *Nucleic Acids Research*, 1989, vol. 17, No. 16, pp. 6463–6471.
A. Edwards et al., *Trans. Assoc. Am. Phys., 102nd Session*, vol. 102:185–194 (1989).
M. Litt et al., *Am. J. Hum. Genetics*, 1989, vol. 44, pp. 397–401.
J. S. Chamberlain, *Nucleic Acids Research*, 1988, vol. 16, No. 23, pp. 11141–11155.
S. S. Chong et al., *Nature Genetics*, 1995, vol. 10. pp. 344–350.
S. M. Pulst et al., *Nature Genetics*, 1996, vol. 14, pp. 269–276.
O. Zhuchenko et al., *Nature Genetics*, 1997, vol. 15, pp. 62–69.
J. Johansson et al., *Human Molecular Genetics*, 1998, vol. 7, No. 2, pp. 171–176.
E. Mornet et al., *Human Molecular Genetics*, 1996, vol. 5, No. 6, pp. 821–825.
Y. H. Fu et al., *Science*, 1992, vol. 255, pp. 1256–1258.
A. Verkerk et al., *Cell*, 1991, vol. 65, pp. 905–914.
K. Snow et al., *Am. J. Hum. Genetics*, 1993, vol. 53, pp. 1217–1228.
S. J. L. Knight et al., *Cell*, 1993, vol. 74, 127–134.
J. E. Parrish et al., *Nature Genetics* 1994, vol. 8, pp. 229–235.
L. J. C. Wong et al., *Am J. Hum. Genetics*, 1995, vol. 56, pp. 114–122.
M. Mahadevan et al., *Science*, 1992, vol. 255, pp. 1253–1255.
D. C. Rubinsztein et al., *Am. J. Hum. Genetics*, 1996, vol. 59, pp. 16–22.
S. E. Andrew et al., *Nature Genetics*, 1993, vol. 4, pp. 398–403.

(List continued on next page.)

*Primary Examiner*—Stephanie Zitomer
(74) *Attorney, Agent, or Firm*—Birch Stewart Kolasch & Birch LLP

(57) ABSTRACT

A process for analyzing length polymorphism in DNA regions wherein the following steps are carried out:

(a) annealing at least one primer pair to the DNA to be analyzed, wherein one of the molecules of the primer pair is substantially complementary to one of the complementary strands of the 5' or 3' flank of a simple or cryptically simple DNA sequence, and wherein the annealing occurs in such an orientation that the synthesis products obtained by a primer-controlled polymerisation reaction with one of said primers can serve as template for annealing the other primer after denaturation;

(b) primer-controlled polymerase chain reaction; and (c) separating and analyzing the polymerase chain reaction products.

41 Claims, 6 Drawing Sheets

OTHER PUBLICATIONS

H. Takano et al., *Am. J. Hum. Genetics*, 1996, vol. 58, pp. 1212–1222.
P. Maciel et al., *Am. J. Hum. Genetics*, 1995, vol. 57, pp. 54–61.
Translation of the Decision issued by the Opposition Division Regarding EP–B 0 438 512 ("Tautz patent") and Minutes of the Oral Proceeding before the Opposition Division (Oct. 26, 2000).
Opposition to the European Patent No. 438 512 (Sep. 24, 1998).
Notice of Opposition in Opposition to European Patent No. 438 512 (Sep. 29, 1998).
European Patent Application No. 89912096.8, Observations by Third Parties in Opposition to European Patent No. 438 512.
Letter to the EPO Opposition Division in Opposition to European Patent No. 438 512 (Aug. 16, 2000).
Letter to the European Patent Office regarding Observations on Oppositions (May 14, 1999) in Opposition to European Patent No. 438 512.
Submissions pursuant to Rule 71a on behalf of Opponent O1 in Opposition to European Patent No. 438 512 (Aug. 25, 2000).
Letter to the European Patent Office regarding Communication of Opposition Division of Apr. 7, 2000 in Opposition to European Patent No. 438 512 (Aug. 25, 2000).
Notice of Opposition Against EP 0 438 512 (Sep. 29, 1998).
Summons to Attend Oral Proceedings Pursuant to Rule 71(1) EPC in Opposition to European Patent No. 483 512 (Apr. 18, 2000).
A. R. La Spada et al., *Nature*, vol. 352, pp. 77–79 (Jul. 1991).
The Huntington's Disease Collaborative Research Group, *Cell*, vol. 72, 971–983 (Mar. 1993).
J. Buxton, *Nature*, vol. 355, pp. 547–548 (Feb. 1992).
Notes of Opposition Division in Opposition to European Patent No. 483 512 (Feb. 2, 2001).
H. G. Harley, *Nature*, vol. 355 (Feb. 6, 1992).
Weber et al., "Genome Mapping" Cold Spring Harbor Meeting Apr. 27$^{th}$ to May 1$^{st}$ 1988 p51a.
Weber et al., A161(0643) *Supplement to Am. J. Hum. Genet.* Sep. 1988.
Weber et al., *Am. J. Hum. Genet.* 1989 44:388–396.
Skolnick et al., *Genomics* 1988 2:273–279.
Wildeman et al., *J. Biol. Chem.* 1986 261:13401–13402.
Schafer et al., *Nucleic Acids Research* 1988 16:5196.
Moyzis et al., *Proc. Natl. Acad Sci.* 1988 85: 6622–6626.
Tautz et al., *Nature* 1986 322:652–656.
Tautz et al., *Nucleic Acids Research* 1984 12:4127–4138.
Fowler et al., *Hum. Genet.* 1988 79:265–272.
Jarman et al., *EMBO Journal* 1986 5: 1857–1863.
Ali et al., *Nucleic Acids Research* 1988 16: 8487–8496.
Nakamura et al., *Science* 1987 235: 1616–1622.
Bell et al., *Nature* 1982 295: 31–35.
Higuchi et al., *Nature* 1988 332: 543–546.
Savatier et al., *J. Mol. Biol.* 1985 182: 21–29.
Jeffreys et al., *Nature* 1985 316: 76–79.
Miesfeld et al., *Nucleic Acids Research* 1981 9: 5931–5947.
Poncz et al., *J. Biol. Chem.* 1983 258: 11599–11609.
Ali et al., *Hum. Genet.* 1986 74: 239–243.
Saiki et al., *Science* 1988 239: 487–491.
Gill, *Nature* 1985 318: 577–579.
Jeffreys, *Nature* 1988 332: 278–281.
Rollo, *Nucleic Acids Res.* 1987 15: 9094.
Ali, *Human Genet.* 1986 74: 239–243.
Marx, *Science* 1988 240: 1408–1410.
Mullis, *Methods Enzymol.* 1987 155: 335.
Jeffreys et al., *Nature* 1985 314: 67–73.
Wolff, *Genomics*, 1988 3: 347–351.
Jarman, *Am J. Hum. Genet.* 1988 43: 249–256.
Shipman, "Detection and Analysis of Human Chromosomes by PCR" (1995) p. 161.
Wrischnik, *Nucleic Acids Res.* 1987 15: 529.
Jeffreys, *Nucleic Acids Research* 1988 16: 10953–10967.
Fowler, *J. Forensic Sciences* 1988 33: 1111–1126.
Levinson et al., *Mol. Biol. And Evolution* 1987 4: 203–221.
Smith et al., *Nature* 1986 321: 674–679.
Warton et al., *Cell* 1985 40: 55–62.
Kan et al., *Proc. Natl. Acad. Sci. USA* 1978 75: 5631–5635.
Tautz et al., *J. Mol. Biol.* 1984 172: 229–235.
Schlotterer et al., *Nucleic Acids Research*, vol. 20, No. 2. pp. 211–215 (1992).
Walsh et al., *Nucleic Acids Research*, vol. 24, No. 14, pp. 2807–2812 (1996).
Bacher et al., *Profiles in DNA*, pp. 3–5, I. Maciver, Ed. (1998).
Bacher et al., *Proc 9$^{th}$Int'l Symposium on Human Identification* pp. 24–37 (1998).

* cited by examiner

TAAGCTTGGGAATCATCTCGCCGACGGGCAGCGATATGGGCATCATGCTCGCCCCGCCCC

AATCCTCGAAGAATAGTGCAATAATGCAAACGATATCACCCCAGCAACAGCAGCAGCAGC

AGCAGCAGCAACAGCAGCAACATCAGCAGCAGCAACAGCAGCAGCAACAGCAGCAGCAGC 202 nt 1 177 nt

AACAGCAGCAGCAACTCGGA*GGCC*TGGAGTTCGGTTCAGAGGGCTTGGACCTGAATGGAT

Hae lll

TTTGTGGATCTCCGGGTAAGTGGTCACTCATGATGGACTCTATGGACTCGCTAACTAGCT

AACTAATCATTCTACCATCCCAACTTGCAGACTCATTTCACTCGGGTCAAATGAATCCGC

CCTCGATACAAAGTTCAAT (SEQ ID NO:5)

FIGURE 2

5′-CTCCCCCACACAAAGAAGTTCTGTTCTCTTCCCTCTACCTTGAT

GAATGCACTGTGA $(TG)_{15\text{-}25}$ACTCGTTCCCAGGTATGGAA-3′

(SEQ ID NO:6)

FIGURE 5

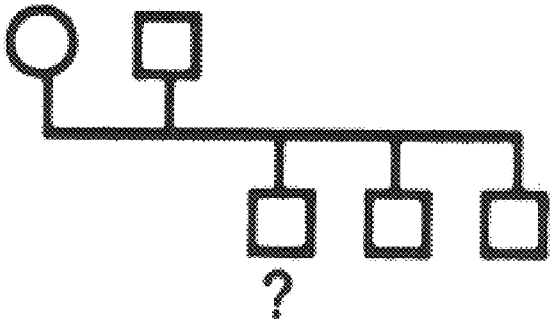
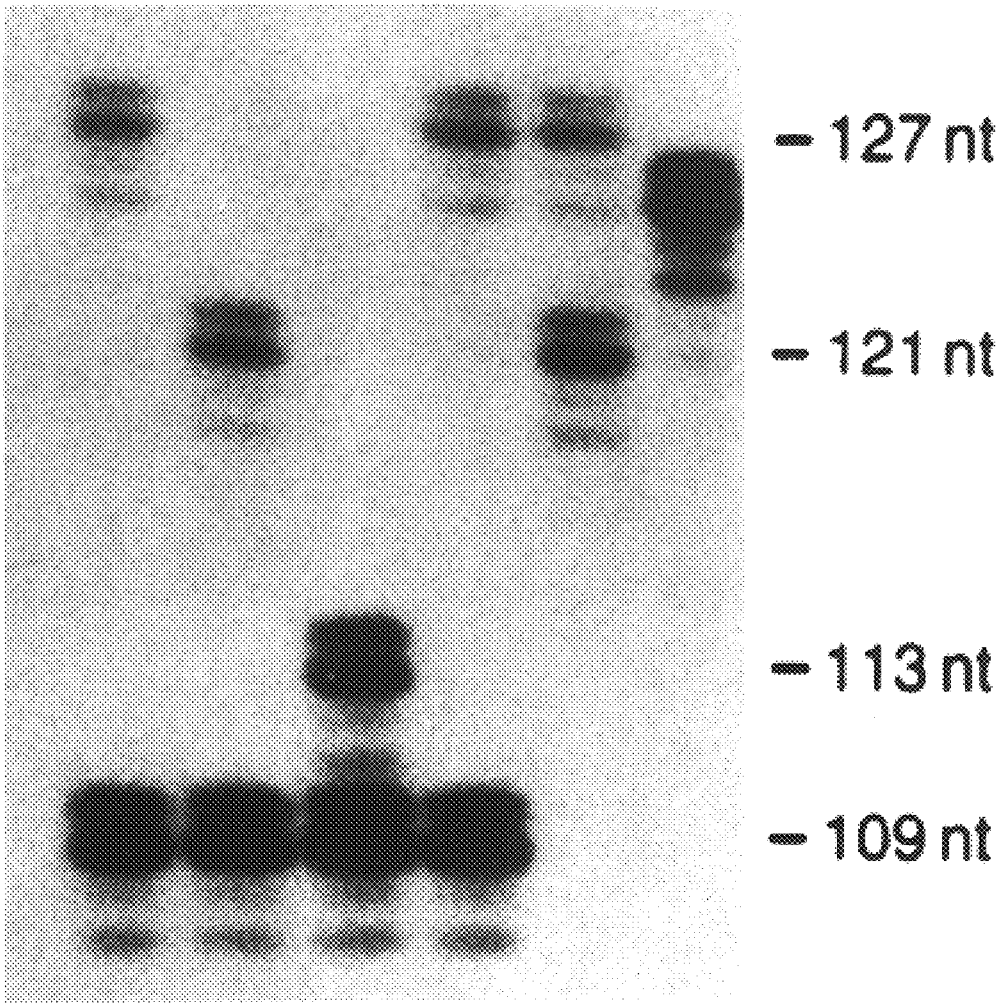
FIG. 6

PROCESS FOR ANALYZING LENGTH POLYMORPHISMS IN DNA REGIONS

Matter enclosed in heavy brackets [ ] appears in the original patent but forms no part of this reissue specification; matter printed in italics indicates the additions made by reissue.

This application is *a reissue application of U.S. Pat. No. 5,766,847, issued Jun. 16, 1998 from application Ser. No. 08/145,617, filed Nov. 4, 1993, which is* a continuation of [application Ser.] *application* No. 07/681,494 filed on Jun. 10, 1991, now abandoned. *Application Ser. No. 07/681,494 is the national stage under 35 U.S.C. §371 of International Application PCT/EP89/01203, filed Oct. 11, 1989 and designating the United States.*

BACKGROUND OF THE INVENTION

1. Field of the Invention

The invention relates to a process for determining identity and kinship of organisms on the basis of length polymorphisms in the regions of simple or cryptically simple DNA sequences.

2. Description of Related Art

All usual processes for the determination of identity and kinship on the basis of DNA length polymorphisms are based on the use of restriction endonucleases. Thereby specific DNA fragments are prepared which are afterwards detected by means of hybridization methods. With these methods either variations in length which have formed between the corresponding recognition sites for restriction endonucleases or variations in length which, have formed due to the lack of certain restriction cleavage sites are analyzed. The first type of polymorphism analysis reveals the variation in length in so-called minisatellite regions (3, 4, 4a, 4b) and/or in regions with specific simple DNA sequences (5). The second analysis in which restriction fragment length polymorphisms (RFLP) due to the presence or absence of a restriction site, are detected can be applied only in specific, empirically found cases and can substantially be used appropriately only in the analysis of genetic diseases.

The disadvantage of both known methods lies in the fact that a hybridization reaction has to be carried out to make the length polymorphic regions visible. This makes the methods time-consuming and expensive. Furthermore, a single analysis using the previous methods does normally not allow any definitive conclusion about the relationship of two samples to be made so that additionally a second independent analysis becomes necessary. Therefore, these processes are not very appropriate for serial examinations and routine testing. Furthermore, the described method are not suitable for automation.

Higuchi et al. (5a) describe a further process for analyzing a length polymorphic locus, comprising a primer-controlled polymerization reaction of certain mitochondrial DNA sequences. This process cannot be used for paternity determination due to the mitochondrial markers used thereby.

Thus, it is the object of the present invention to provide a method for analyzing length polymorphisms in DNA regions which is highly sensitive, achieves reliable results without being time-consuming, is furthermore appropriate for serial examinations and routine testing and can optionally also be carried out automatically.

According to the invention this problem is solved by providing a process for determining identity and kinship of organisms on the basis of length polymorphisms in DNA regions, which process comprises the following steps:

(a) annealing at least one primer pair to the DNA to be analyzed, wherein one of the molecules of the primer pair is substantially complementary to one of the complementary strands of the DNA flanking a simple or cryptically simple DNA sequence on either the 5' or the 3' side, and wherein the annealing occurs in such an orientation that the synthesis products obtained by a primer-directed polymerization reaction with one of said primers can serve as template for annealing the other primer after denaturation;

(b) primer-directed polymerase chain reaction; and (c) separating and analyzing the polymerase chain reaction products.

In this process the individual primer molecules of the primer pairs are annealed to the DNA region to be analyzed at a distance of 50 to 500 nucleotides apart so that they encompass it at the given distance. Thereby the DNA region to be analyzed is surrounded by the hybridization molecules of the primer pair.

The primer-directed chain reaction is known as such from EP-A2 0 200 362 (1), from EP-A1 0 237 362 (1a) and from (2). It refers to a process for amplification of specific DNA fragments in which a PCR (polymerase chain reaction) is carried out. In this process the specific amplification is achieved by using oligonucleotide primers flanking the target-molecule in an anti-parallel manner. Thereby in a template-dependent extension of the primers by a polymerase DNA fragments are synthesized which themselves are again available as templates for a new cycle of primer extension. The DNA synthesis is performed by heat denaturation of the starting molecules, followed by hybridization of the corresponding primers and by chain extension with a polymerase. By means of a further heat denaturation a following cycle is then performed. Thereby the specifically amplified region grows in an exponential way and finally a fragment detectable by normal gel electrophoresis is formed. The length of this fragment is determined by the length of the primers and the intermediate region and is similar or equal to the sum of the lengths of the primers and the intermediate region. The use of thermostable synthesis components allows control of the process by simple and easily automated heating and cooling cycles.

By "antiparallel flanking" of the target molecule by oligonucleotide primers one understands the hybridizing of one of both primers of a primer pair each to the complementary strands of the target molecule so that the 3' ends of the primer pair point at each other.

In (15) Marx describes different applications of the PCR process.

Rollo et al. describe in (16) the use of the PCR process for distinguishing between various species of the plant pathogenic fungus Phoma.

The use of simple and cryptically simple DNA sequences in the fragment of PCR processes for determining identity and kinship of organisms is not described in any of these references.

SUMMARY OF THE INVENTION

Simple and cryptically simple DNA sequences are repetitive components of all eukaryotic genomes which to some extent can be found also in prokaryotic genomes (6–9). Thereby simple DNA sequences comprise short DNA motifs containing at least one nucleotide and not more than approximately 6 to 10 nucleotides arranged as a dozen to approximately one hundred tandem repeats. These simple DNA sequences have been found by hybridization with synthetic DNA sequences and by direct sequencing in all hitherto analyzed eukaryotic genomes and also in the human genome (8, 10). All possible permutations of short motifs can presumably be found therein in different frequency (9). Cryptically simple DNA sequences are characterized by a more than accidentally frequent, but irregularly direct repeat of short DNA motifs (9). Cryptically simple DNA sequences are normally only found indirectly in already sequenced DNA regions by means of a corresponding computer programme. They are, however, at least just as frequent or even more frequent than simple DNA sequences. The simple and cryptically simple DNA sequences are likely to have formed by genomic mechanisms having the tendency to duplicate once more already existing short duplications of any DNA sequence motifs or to partly delete in any DNA sequence motifs longer regions of already existing simple or cryptically simple DNA sequences (8–10). Therefore one can start from the assumption that these regions are usually length polymorphic. The process according to the invention is based on this length polymorphism.

Simple or cryptically simple DNA sequences that are suitable for the process according to the invention can be found with or without a computer programme in DNA sequences that are already known (9). A simple or cryptically simple DNA sequence is suitable for use in the method of the present invention if it has a length of approximately 20 to 300 nucleotides and if it is flanked by random sequences, i.e. DNA sequences without internal repeats. From the region of DNA sequences without internal sequence repeats fragments that flank the simple or cryptically simple DNA sequence are selected. Suitable complementary synthetic oligonucleotides are then prepared which can hybridize to the flanking DNA sequences. An oligonucleotide is suitable for this purpose if its nucleotide composition and its nucleotide sequence can be found most probably only once in the genome to be examined, thus being specific to the DNA region to be individually analyzed.

In the process according to the invention, preferably length polymorphisms of simple or cryptically simple DNA sequences are examined.

When examining length polymorphisms of simple or cryptically simple DNA sequences substantially composed of tri-nucleotide motifs, so-called "slippage"-artifacts are avoided. Slippage-artifacts are more frequently found, for example, in simple or cryptically simple DNA sequences composed of dinucleotide motifs. Thereby reaction products are formed which are shorter than the desired main product (cf. Example 4). These artificial bands are possibly difficult to distinguish from "real" bands which complicates the interpretation of the results. When using simple or cryptically simple tri-nucleotide sequences, these artifacts do not or only rarely occur (cf. Example 3).

In a particularly preferred embodiment of the process according to the invention the simple or cryptically simple DNA sequence is substantially composed of the trinucleotide motif $^{5'}CAG^{3'}/^{5'}CTG^{3'}$.

In the process according to the invention two primer pairs are preferably employed. In a particularly preferred embodiment 2 to 50 primer pairs are employed.

Preferably the primers used in the process according to the invention have a length of 15 to 25 nucleotides.

In a preferred embodiment of the process according to the invention when using several primer pairs the individual primer pairs are selected in such a way that the corresponding specific polymerase chain reaction products of the individual primer pairs are separable into individual bands on a suitable gel.

In another preferred embodiment of the process according to the invention the detection of the specific polymerase chain reaction products is carried out by radioactive labelling or by non-radioactive labelling, e.g. with fluorescent dye-stuff.

The labelling of the oligonucleotide pairs can be carried out radioactively or with a fluorescent dyestuff, as described in (12).

Furthermore, kits with which the process according to the invention can be carried out are a subject matter of the present invention. The primers contained therein are optionally labelled radioactively, e.g. with $^{35}S$ or $^{14}C$, or fluorescently.

The synthesis products obtained in the process according to the invention can be separated using high-resolution gel systems, such as usual sequencing gels. At the same time also the length of the synthesis products can be determined. Polymorphisms which are formed by insertions or deletions of individual or several motifs of the simple or cryptically simple DNA sequence are recognizable by an altered position of the synthesis products in the gel. With an appropriate selection of the primer pairs and with an appropriate resolution capacity of the gel system approximately 20 to 50 independent polymorphic regions can be simultaneously examined. Thus, the identity of an individual can be reliably ascertained due to the individual combination of length distributions of the synthesis products obtained.

If no appropriate simple or cryptically simple DNA sequences are known in the DNA regions to be examined, they can be identified as follows:

A genomic DNA to be examined is subjected to a partial restriction cleavage. Restriction enzymes are used that do normally not cleave in simple or cryptically simple DNA sequences. The DNA fragments obtained are cloned in a suitable vector, e.g. in lambda phage derivatives or in M13-phages and are then screened by usual methods for simple or cryptically simple DNA sequences; cf. (11). The probe molecules used are synthetic DNA molecules containing various permutations of simple or cryptically simple DNA sequences. Thus, hybridizing plaques can be identified. Then the recombinant DNA contained therein can be isolated and characterized by sequencing. The DNA sequence thus obtained can then be screened for DNA sequences which are suitable for the testing procedure according to the invention.

The process according to the invention was carried out with Drosophila-DNA as a model system. As simple and cryptically simple DNA sequences are present in all eukaryotic genomes and to some extent also in prokaryotic genomes, one can assume that the results achieved with the Drosophila model system can also be achieved in the analysis of other genomes, particularly in the examination of the human genome.

Therefore the process according to the invention is suitable for the determination of identity and kinship of organisms, for example of human beings.

In human beings paternity and forensic tests for establishing the identity of delinquents can be carried out with the process according to the invention; cf. also Example 4.

In addition to the determination of identity of individuals the process is also suitable to determine the course of hereditary propagation of genetic diseases for which the locus is known and sequenced. For this purpose one or several simple or cryptically simple sequences are selected which are located in or next to the locus to be analyzed. The specific length pattern of these regions is correlated with the mutated locus, as is common practice with known RFLP-markers; cf. (14). With the families concerned on the basis of this information genetic advice can be given or prenatal diagnosis can be made in a manner analogous to that known for RFLP-markers. The use of the process according to the invention for this purpose makes sense especially because it is based on DNA regions which are polymorphic in all foreseeable probability whereas the RFLP-analysis is dependent on accidentally found variations which are often far away from the locus itself which reduces the certainty of diagnosis.

The process according to the invention is further suitable for determining polymorphisms in simple or cryptically simple DNA sequences of animals and plants. Therefore, in animal breeding, e.g. of horses, dogs or cattle, and kinship to high-grade breeding individuals can be reliably proved.

To sum up, it can be said that the advantage of the process according to the invention vis-a-vis the hitherto known processes lies in its broad applicability, rapid practicability and in its high sensitivity. The amplification step taken for the length polymorphic simple or cryptically simple DNA sequences in the process according to the invention makes it superfluous to take an independent ascertaining step, such as a subsequent hybridization reaction. Therefore the process according to the invention is particularly well suited for automation and for routine testing and serial examination.

Approximately 20,000 independent phage clones were plated out on a 12 by 12 cm plate and hybridized with a probe molecule containing the simple trinucleotide sequence CAG/CTG. 300 to 400 positive signals are thus obtained. The positive signals are recognizable as blackening.

FIG. 2: Sequence (SEQ. ID NO. 5) of the region tested for polymorphism in Example 2.

The regions to which complementary oligonucleotides were synthesized are underlined with a wavy line. The region of the simple DNA sequence is underlined with a double line. The direct repeat of 8 nucleotides is marked with two arrows. The HaeIII-cleavage site is marked in italics.

Figure 3:
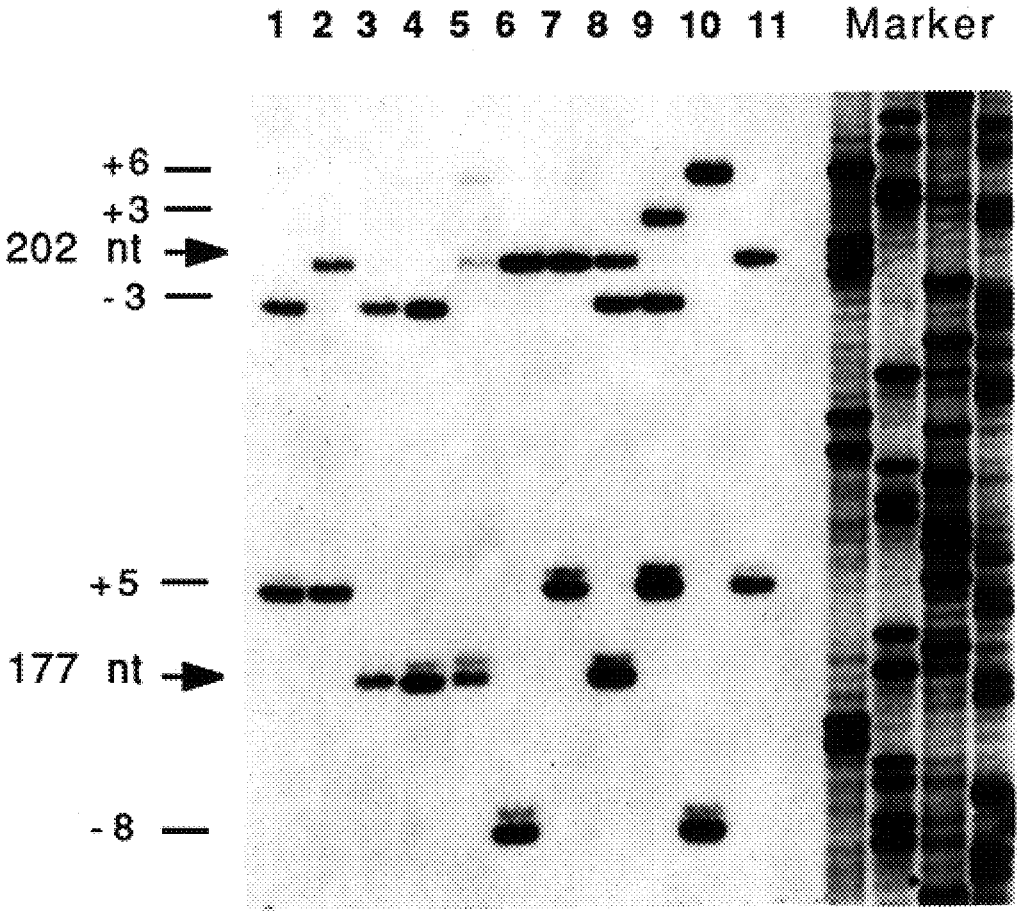

FIG. 3: Analysis of the length variations of 11 wild type strains in Drosophila The DNA sequences amplified by means of PCR and cleaved with HaeIII are shown in lanes 1 to 11. On the right side a sequencing reaction is shown serving as length marker. The position of the fragments to be expected is marked with arrows on the left side. The positions of the fragment classes additionally observed is marked with lines.

Figure 4:
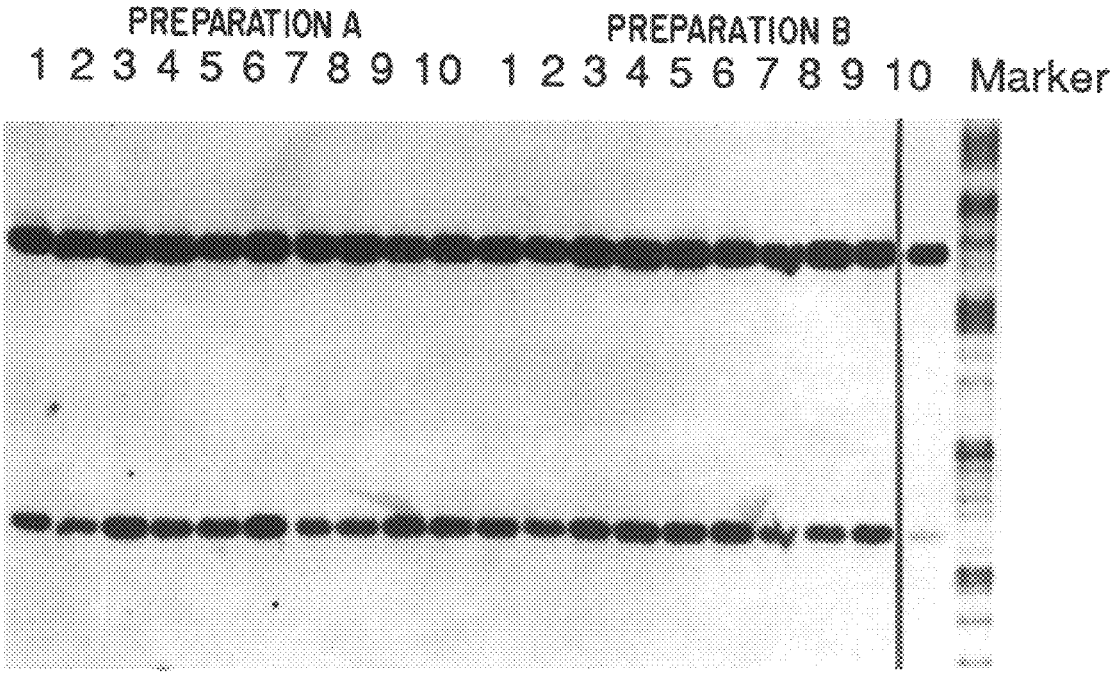

FIG. 4: Test for Reproducibility

Ten independent PCR-reaction mixtures using the DNA preparation "A" of the Drosophila strain No. 3 were applied on the left side, ten independent PCR-reaction mixtures using the DNA preparation "B" of the Drosophila strain No. 3 were applied on the right side. On the very right side marker fragments from a sequencing reaction are applied. All test bands observed are identical.

FIG. 5: Sequence (SEQ IN NO. 6) of the DNA region used in Example 4.

The regions to which complementary oligonucleotides were synthesized are underlined with a wavy line.

FIG. 6: Paternity analysis in human beings.

The DNA fragments amplified by means of PCR and separated on the gel are shown. In the first lane the DNA of the mother, in the following lanes the DNA of the father to be tested as well as of the three tested children have been applied. In the sixth lane (marked with "C") a control-DNA has been applied which is to indicate only the size categories. The main bands and their size categories are marked on the right side.

DETAILED DESCRIPTION OF THE INVENTION

The examples illustrate the invention.

EXAMPLE 1

Isolation of Clones Containing Simple DNA Sequences

Drosophila-DNA is completely cleaved with the restriction endonuclease EcoRI and the resulting fragments are cloned into the lambda vector 641. A more detailed description of the methods used can be found in (11). By this way a gene library is obtained of which about 20,000 phages are plated out. The corresponding independent plaques are transferred to a nitrocellulose filter and hybridized with a probe molecule containing the simple DNA sequence motif CAG/CTG.

The filters are hybridized and washed at 65° C. The hybridizing solution contains 5 × SSPE, 5 × Denhardt's solution, 0.1% sodium dodecyl sulfate (SDS) and approximately $1\times10^6$ cpm/ml of radioactively labelled ($^{32}P$) DNA as probe molecule. The wash solution contains 2 × SSPE and 0.1% SDS (the reaction product of Denhardt's solution and SSPE is described in (11)).

Figure 1:
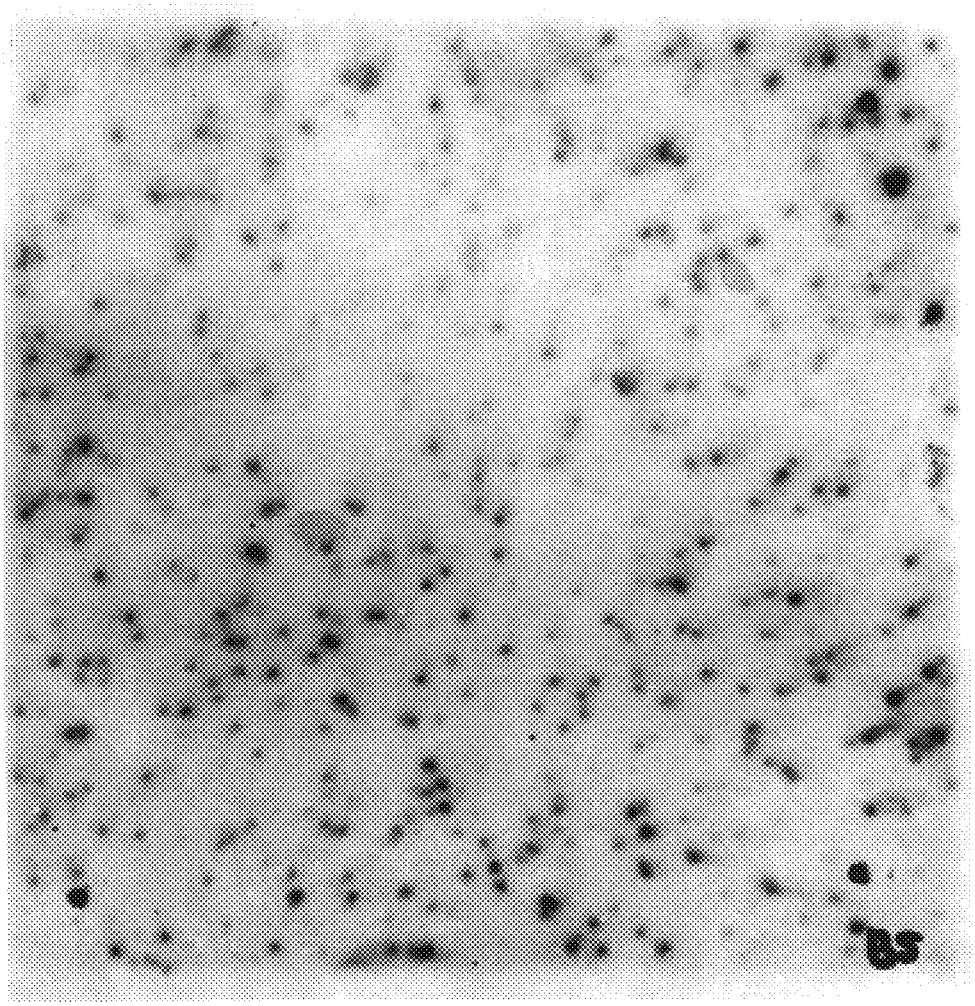
FIG. 1: Hybridization of a Gene Library with a simple DNA sequence as probe molecule.

About 300 to 400 of the plaques formed show a positive signal; cf. FIG. 1. Some of these plaques are purified, DNA is isolated and sequenced. In the obtained DNA sequences regions can be identified containing the simple DNA sequence CAG/CTG; cf. (7).

EXAMPLE 2

Detection of Length Polymorphisms

For this experiment the DNA sequence illustrated in FIG. 2 and published in (13) was chosen. Two oligonucleotides with the following sequences were synthesized:

Oligonucleotide 1 (SEQ. ID No. 1): 5'-TAAGCTT GGGAATCA-3'

Oligonucleotide 2 (SEQ. ID No. 2): 5'-ATTGAAC TTTGTATC-3'

These DNA sequences are located immediately at the beginning or at the end of the sequence shown in FIG. 2. For use as primers the synthesized oligonucleotides are labelled with $^{32}P$ at their 5' end. Then a PCR reaction with the labelled primers is carried out. On the whole 20 cycles are carried out by denaturating at 95° C. for 90 seconds, hybridizing at 45° C. for 90 seconds and then synthesizing at 72° C. for 120 seconds. As DNAs to be examined the genomic DNAs of 11 wild type strains of Drosophila melanogaster from various regions all over the world are employed. These Drosophila wild type strains originally are descendants of individual fertilized females and have been collected during the last 10 years. After the PCR reaction the amplified fragments are cleaved with the restriction endonuclease HaeIII. This should normally yield two fragments having a length of 202 and 177 nucleotides, respectively. This step is normally not necessary for routine experiments. Here it only serves to refine the analysis. The resulting fragments are separated on a 5% sequencing gel, the gel is subsequently dried and an X-ray film is exposed to the dried gel. Both DNA fragments expected show a marked polymorphism in the various Drosophila wild type strains. The 202 nucleotide fragment which contains the simple DNA sequence shows four different size categories; see FIG. 3. These size categories are shifted by three nucleotides each. Starting from frameshifts within the repeat of the trinucleotides this is to be expected. In three cases two different bands appear at the same time; cf. FIG. 3, lanes 5, 8 and 9. This can be explained by the fact that in diploid organisms each locus is to be found twice and can be represented by different alleles (so-called balanced polymorphism). The band of the 177 nucleotide fragment shows three different size categories being 5 or 8 nucleotides apart; cf. FIG. 3. The band which is shorter by 8 nucleotides presumably resulted from a deletion of the repeat of 8 nucleotides labelled in the DNA sequence. The origin of the longer band is unclear. These deletions or insertions correspond to those that can be expected in the region of a cryptically simple DNA sequence.

The majority of the strains examined in this simple experiment are readily distinguishable from one another. Only strains 2, 7 and 11 as well as 3 and 4 cannot be distinguished from each other. To distinguish these strains one would therefore employ further primer pairs. For example, 20 to 50 independent DNA regions could be tested, in order to allow a definite identification. As the size categories of the fragments of the individual Drosophila wild type strains are homogenous per se, one has to start from the assumption that the polymorphisms observed are not so frequent that it would no longer be possible to ascertain a kinship. The Drosophila wild type strains all descend from one single original pair and the DNA of several 100 individuals was combined for the test. If a change of the pattern had taken place within these "families", one should expect more than maximal two bands. This is, however, not the case here. From this follows that the length categories observed are stable for at least some dozens of generations.

EXAMPLE 3

Test for Reproducibility

The variations in length observed could also be caused by polymerase errors during the experiment. In order to exclude this possibility and to simultaneously prove the general reproducibility, the experiment carried out in Example 2 is repeated with two different DNA preparations of the Drosophila strains No. 3 in 10 independent reaction mixtures. It can be taken from FIG. 4 that all reaction mixtures lead to the same bands. Similar experiments were also carried out for different loci. In no case, however, a change of the band length could be observed. This shows that the process is reliably reproducible.

EXAMPLE 4

Paternity Test in Human Beings

A primer pair is used which flanks a sequential region from the autosomal human heart muscle actin gene. This sequence contains a simple sequence with a GT/CA dinucleotide repeat structure (FIG. 5). As primers the following oligonucleotides are used:

Primer 1 (SEQ ID No. 3): 5'-CTCCCCC ACACAAAGAAG-3'

Primer 2 (SEQ ID No. 4): 5'-TTCCATA CCTGGGAACGA-3'

Primer 2 is labelled at its 5' end with $^{32}P$ and both oligonucleotides are then used for a PCR reaction. On the whole 25 cycles with a denaturation phase of 1 min. at 94° C., an hybridizing phase of 2 min. at 45° C. and a synthesis phase of 1 min at 72° C. (last synthesis phase for 5 min) are carried out. The reaction products are then separated on a 6% denaturating acrylamide gel, the gel is dried and exposed. The result can be seen in FIG. 6. Each of the tested individuals shows two main bands (for explanation of the further bands, see below), i.e. it is heterozygous for different length variants of this locus. Mother and father have the length variant "109 nt" in common, they do, however, differ in the other variant, with the mother having a "127 nt" and the father a "121 nt" variant. The children must have inherited one of each of these variants from father and mother. For two of the children this is actually the case, whereas the third child (labelled with "?") shows a new "113 nt" variant, which can neither be derived from the mother nor from the tested father. Therefore, one has to assume that this child had another father.

In lane "C" a cloned control-DNA having only one length variant has also been treated. Like the other samples it shows a main band and several secondary bands. The secondary bands are caused by PCR artifacts formed during the amplification. In this context, there are two types of artifacts. The first type results from the fact that the Taq-polymerase has the tendency to attach an additional nucleotide to the completely synthesized DNA strand. Thereby the band is formed which runs a nucleotide above the main band. This effect varies from reaction to reaction, but does not disturb the analysis of the band pattern. A second type of artifact is formed by "slippage" during the amplification process. This leads to the bands which can be seen at the dinucleotide distance below the main bands. These artifact bands could have a disturbing effect on the analysis, if they overlap actual length variants.

Simple sequences with trinucleotide repeat motifs do not show these artifact bands (cf. Example 2), as with these sequences "slippage" occurs less frequently during amplification.

LITERATURE

EP-A2 0 200 362

1.a EP-A1 0 237 362

2. R. K. Saiki et al., Science 239 (1988), 487–491

3. A. J. Jeffreys et al., Nature 314 (1985), 67–73

4. A. J. Jeffreys et al., Nature 316 (1985), 76–79

4.a Gill et al., Nature 318 (1985), 577–579

4.b Nakamura et al., Science 235 (1987), 1616–1622

5. EP 87 11 6408.3

5.a Higuchi et al., Nature 332 (1988), 543–546

6. D. Tautz, PhD-Thesis (Doktorarbeit) University of T übingen (1983)

7. D. Tautz and M. Renz, J. Mol. Biol. 172 (1984), 229–235

8. D. Tautz and M. Renz, Nucleic Acids Research 12 (1984), 4127–4138.

9. D. Tautz et al., Nature 332 (1986), 652–656

10. G. Levinson and G. A. Gutman, Mol. Biol. and Evolution 4 (1987), 203–221

11. T. Maniatis, E. F. Fritsch and J. Sambrook, "Molecular Cloning, a Laboratory Manual", Cold Spring Harbor Laboratory, New York, 1982

12. L. M. Smith et al., Nature 321 (1986), 674–679

13. K. A. Wharton et al., Cell 40 (1985), 55–62

14. Y. W. Kan and A. M. Dozy, Proc. Natl. Acad. Sci. USA 75 (1978), 5631–5635

15. Marx, Science 240 (1988), 1408–1410

16. Rollo et al., Chem. Abstr. 108(1) (1988), 154, Abstract No. 1552s

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 1:

TAAGCTTGGG AATCA 15

(2) INFORMATION FOR SEQ ID NO: 2:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 2:

ATTGAACTTT GTATC 15

(2) INFORMATION FOR SEQ ID NO: 3:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 3:

CTCCCCCACA CAAAGAAG 18

(2) INFORMATION FOR SEQ ID NO: 4:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 4:

TTCCATACCT GGGAACGA 18

-continued

```
(2) INFORMATION FOR SEQ ID NO: 5:

     (i) SEQUENCE CHARACTERISTICS:
          (A) LENGTH: 379 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO: 5:

TAAGCTTGGG AATCATCTCG CCGACGGGCA GCGATATGGG CATCATGCTC GCCCCGCCCC     60

AATCCTCGAA GAATAGTGCA ATAATGCAAA CGATATCACC CCAGCAACAG CAGCAGCAGC    120

AGCAGCAGCA ACAGCAGCAA CATCAGCAGC AGCAACAGCA GCAGCAACAG CAGCAGCAGC    180

AACAGCAGCA GCAACTCGGA GGCCTGGAGT TCGGTTCAGA GGGCTTGGAC CTGAATGGAT    240

TTTGTGGATC TCCGGGTAAG TGGTCACTCA TGATGGACTC TATGGACTCG CTAACTAGCT    300

AACTAATCAT TCTACCATCC CAACTTGCAG ACTCATTTCA CTCGGGTCAA ATGAATCCGC    360

CCTCGATACA AAGTTCAAT                                                 379


(2) INFORMATION FOR SEQ ID NO: 6:

     (i) SEQUENCE CHARACTERISTICS:
          (A) LENGTH: 107 base pairs
          (B) TYPE: nucleic acid
          (C) STRANDEDNESS: single
          (D) TOPOLOGY: linear

    (ii) MOLECULE TYPE: DNA (genomic)

    (ix) FEATURE:
          (A) NAME/KEY: repeat_region
          (B) LOCATION: 58..87
          (D) OTHER INFORMATION: /rpt_type= "other"
               /label= tg_DINUCLEOTIDE

    (ix) FEATURE:
          (A) NAME/KEY: -
          (B) LOCATION: 58..87
          (D) OTHER INFORMATION: /label= TG_DINUCLEOTIDE
               /note= "THIS STRETCH OF TG DINUCLEOTIDES RANGES IN
               SIZE FROM 15 DINUCLEOTIDES TO 25 DINUCLEOTIDES
               ((TG)15 TO 25)"

    (xi) SEQUENCE DESCRIPTION: SEQ ID NO: 6:

CTCCCCCACA CAAAGAAGTT CTGTTCTCTT CCCTCTACCT TGATGAATGC ACTGTGATGT     60

GTGTGTGTGT GTGTGTGTGT GTGTGTGACT CGTTCCCAGG TATGGAA                  107
```

We claim:

1. A method for determining length polymorphisms in a simple or cryptically simple sequence in one or more DNA regions of one or more subjects, which comprises:

a) providing at least one DNA sample, comprising a template DNA having a nucleotide sequence that includes a simple or cryptically simple sequence *comprising trinucleotide repeats*, from at least one subject;

b) annealing at least one primer pair to the template DNA of each of said DNA samples, wherein said primer pair is composed of a first primer complementary to a nucleotide sequence flanking the simple or cryptically simple DNA sequence on the 5' side of said simple or cryptically simple DNA sequence and a second primer complementary to a nucleotide sequence flanking the simple or cryptically simple DNA sequence on the 3' side of said simple or cryptically simple DNA sequence; wherein said first and second primers each anneal to a single site in said template DNA and the sequence of the template DNA between the sites where said primers anneal is 50 to 500 nucleotides in length;

c) performing at least one primer-directed polymerase chain reaction upon said template DNA having said primers annealed thereto, so as to form at least one polymerase chain reaction product;

d) separating the products of each polymerase chain reaction according to their lengths; *and* e) analyzing the *lengths of the* separated products to determine the length polymorphisms of the simple or cryptically simple sequences.

[2. The method according to claim 1, wherein each simple or cryptically simple DNA sequence comprises at least one trinucleotide motif.]

3. The method according to claim 1, wherein [each simple or cryptically simple DNA sequence contains] the *trinucleotide repeat* motif *is* CAG/CTG.

4. The method according to claim 1, wherein at least 2 primer pairs are used.

5. The method according to claim 1, wherein between 2 and 50 primer pairs are used.

6. The method according to claim 1, wherein each of the primers has a length ranging between 15 and 25 nucleotides.

7. The method according to claim [2] *1*, wherein the annealing position of the primers of each pair is selected such that each of the primer-directed polymerase chain reaction products are separable one from the other as individual bands on a suitable electrophoretic gel.

8. The method according to claim 1, wherein the product of each primer-directed polymerase chain reaction is labelled by a radioactive label.

9. The method according to claim 1, wherein the product of each primer-directed polymerase chain reaction is labelled by a non-radioactive label.

10. The method according to claim 9, wherein said non-radioactive label is a fluorescent label.

11. The method according to claim 1, wherein said simple or cryptically simple DNA sequence is located adjacent to or within a genetically defined locus such that said simple or cryptically simple DNA sequence can serve as a marker for said locus.

12. A kit for performing the method of claim 1, comprising:

a) at least one vessel containing an equimolar mixture of primers constituting between 1 and 50 of said primer pairs;

b) a vessel containing a polymerizing enzyme suitable for performing a primer-directed polymerase chain reaction;

c) a vessel containing the deoxynucleotide triphosphates adenosine, guanine, cytosine and thymidine;

d) a vessel containing a buffer solution suitable for performing a polymerase chain reaction, or a concentrate of said buffer solution;

e) a vessel containing a template DNA that has a nucleotide sequence including a simple or cryptically simple sequence for assaying positive performance of the method, *wherein each simple or cryptically simple DNA sequence comprises at least one trinucleotide motif.*

13. The kit of claim 12, wherein at least one primer of each primer pair is labelled with a fluorescent or a radioactive label.

14. The method of claim 1, wherein the kinship of at least two subjects is determined by comparing length polymorphisms determined in step (e).

*15. A method for analyzing length polymorphisms in at least one locus in an DNA sample obtained from at least one subject, wherein said DNA sample comprises a DNA template having at least one locus comprising a simple or cryptically simple DNA sequence, said method comprising:*

*a) annealing said DNA template with at least one pair of primers, wherein said primer pair is composed of a first primer complementary to a nucleotide sequence flanking said simple or cryptically simple DNA sequence on the 5′ side of said simple or cryptically simple DNA sequence and a second primer complementary to a nucleotide sequence flanking the simple or cryptically simple DNA sequence on the 3′ side of said simple or cryptically simple DNA sequence; wherein said first and second primers each anneal to a single site in said DNA template and wherein the annealing sites are separated by 50 to 500 nucleotides of template DNA;*

*b) performing at least one primer-directed polymerase chain reaction upon said template DNA having said primers annealed thereto, so as to form at least one polymerase chain reaction product;*

*c) separating the products of each polymerase chain reaction according to their lengths; and*

*d) analyzing the lengths of the separated products to determine the length polymorphisms of said simple or cryptically simple sequences;*

*wherein said simple or cryptically simple sequence has a repeat length of 3 to 10 nucleotides.*

*16. The method of claim 15, wherein said simple or cryptically simple sequence has a repeat length of 3 to 6 nucleotides.*

*17. The method of claim 15, wherein said simple or cryptically simple sequence has a repeat length of 3 nucleotides.*

*18. The method of claim 15, wherein at least two primer pairs are used.*

*19. The method of claim 15, wherein the kinship of at least two subjects is determined by comparing the length polymorphisms determined in step (d).*

*20. The method of claim 16, wherein the kinship of at least two subjects is determined by comparing the length polymorphisms determined in step (d).*

*21. The method of claim 15, further comprising (e) comparing the length polymorphisms determined in step (d) to numerical values of length polymorphisms for said at least one locus.*

*22. The method of claim 16, further comprising (e) comparing the length polymorphisms determined in step (d) to numerical values of length polymorphisms for said at least one locus.*

*23. The method of claim 15, wherein 2 to 50 primer pairs are used.*

*24. The method according to claim 15, wherein each of the primers has a length of 15 to 25 nucleotides.*

*25. The method according to claim 15, wherein the annealing position of the primers of each pair is selected such that each of the products of the primer-directed polymerase chain reaction is separable one from the other as individual bands on a suitable electrophoretic gel.*

*26. The method according to claim 15, wherein the product of each primer-directed polymerase chain reaction is labeled by a radioactive label.*

*27. The method according to claim 15, wherein the product of each primer-directed polymerase chain reaction is labeled by a non-radioactive label.*

*28. The method according to claim 27, wherein said non-radioactive label is a fluorescent label.*

*29. The method according to claim 15, wherein said simple or cryptically simple DNA sequence is located adjacent to or within a genetically defined locus such that said simple or cryptically simple DNA sequence can serve as a marker for said locus.*

*30. The method of claim 15, wherein said simple or cryptically simple sequence has a repeat length of 3 to 6 nucleotides, each of said primers has a length of 15 to 25 nucleotides and the kinship of at least two subjects is determined by comparing the length polymorphisms determined in step (d).*

*31. The method of claim 15, wherein said simple or cryptically simple sequence has a repeat length of 3 to 6 nucleotides, each of said primers has a length of 15 to 25 nucleotides and wherein 2 to 50 primer pairs are used.*

*32. The method of claim 29, wherein said simple or cryptically simple sequence has a repeat length of 3 to 6 nucleotides, each of said primers has a length of 15 to 25 nucleotides and 2 to 50 primer pairs are used.*

*33. The method of claim 30, wherein said simple or cryptically simple sequence has a repeat length of 3 nucleotides.*

*34. The method of claim 32, wherein said simple or cryptically simple sequence has a repeat length of 3 nucleotides.*

*35. A kit for performing analysis of polymorphism in simple or cryptically simple sequences, comprising:*

*a) at least one vessel containing a mixture of primers constituting 1 to 50 primer parts; wherein each of said primer pairs is composed of a first primer complementary to a nucleotide sequence flanking said simple or cryptically simple DNA sequence on the 5′ side of said simple or cryptically simple DNA sequence and a second primer complementary to a nucleotide sequence flanking the simple or cryptically simple DNA sequence on the 3′ side of said simple or cryptically simple DNA sequence; wherein said first and second primers each anneal to a single site in said DNA template and wherein the annealing sites are separated by 50 to 500 nucleotides of template DNA;*

*b) a vessel containing a template DNA that has a nucleotide sequence including a simple or cryptically simple sequence for assaying positive performance of the method.*

*36. The kit of claim 35, wherein at least one primer of each primer pair is labeled with a fluorescent or a radioactive label.*

*37. The kit of claim 35, wherein said simple or cryptically simple sequence has a repeat length of 3 to 6 nucleotides and each of said primers has a length of 15 to 25 nucleotides.*

*38. The kit of claim 35, wherein said simple or cryptically simple DNA sequence is located adjacent to or within a genetically defined locus such that said simple or cryptically simple DNA sequence can serve as a marker for said locus.*

*39. The kit of claim 38, wherein at least one primer of each primer pair is labeled with a fluorescent or a radioactive label.*

*40. A method for determining length polymorphisms in a simple or cryptically simple sequence in one or more DNA regions of one or more subjects, which comprises:*

*a) providing at least one DNA sample, comprising a template DNA consisting essentially of a nucleotide sequence that includes i) a simple or cryptically simple sequence having a trinucleotide repeat motif and ii) nucleotide sequences flanking the simple or cryptically simple sequence, from at least one subject;*

*b) annealing at least one primer pair to the template DNA of each of said DNA samples, wherein said primer pair is composed of a first primer complementary to the nucleotide sequence flanking the simple or cryptically simple DNA sequence on the 5′ side of said simple or cryptically simple DNA sequence and a second primer complementary to the nucleotide sequence flanking the simple or cryptically simple DNA sequence on the 3′ side of said simple or cryptically simple DNA sequence; wherein said first and second primers each anneal to a single site in said template DNA and the sequence of the template DNA between the sites where said primers anneal is 50 to 500 nucleotides in length;*

*c) performing at least one primer-directed polymerase chain reaction upon said template DNA having said primers annealed thereto, so as to form at least one polymerase chain reaction product;*

*d) separating the products of each polymerase chain reaction according to their lengths;*

*e) analyzing the lengths of the separated products to determine the length polymorphisms of the simple or cryptically simple sequences.*

*41. A method for analyzing polymorphism in at least one locus in an DNA sample comprising a DNA template, said method comprising:*

*a) annealing said DNA template with at least one pair of primers, wherein said primer pair is composed of a first primer complementary to a nucleotide sequence flanking said simple or cryptically simple DNA sequence on the 5′ side of said simple or cryptically simple DNA sequence and a second primer complementary to a nucleotide sequence flanking the simple or cryptically simple DNA sequence on the 3′ side of said simple or cryptically simple DNA sequence; wherein said first and second primers each anneal to a single site in said DNA template and wherein the annealing sites are separated by 50 to 500 nucleotides of template DNA;*

*b) performing at least one primer-directed polymerase chain reaction upon said template DNA having said primers annealed thereto, so as to form at least one polymerase chain reaction product;*

*c) separating the products of each polymerase chain reaction product according to their lengths; and*

*d) analyzing the lengths of the separated products to determine the length polymorphisms of said simple or cryptically simple sequences,*

*wherein said DNA template includes at least one sequence consisting essentially of a simple or cryptically simple DNA sequence having a repeat motif length of 3 to 10 nucleotides and nucleotide sequences flanking said simple or cryptically simple DNA sequence effective for annealing said at least one pair of primers.*

*42. A kit for analyzing polymorphism in at least one locus in an DNA sample, comprising:*

*a) at least one vessel containing a mixture of primers constituting between 1 and 50 of said primer pairs;*

*b) a vessel containing a polymerizing enzyme suitable for performing a primer-directed polymerase chain reaction;*

*c) a vessel containing the deoxynucleotide triphosphates adenosine, guanine, cytosine and thymidine;*

*d) a vessel containing a buffer solution for performing a polymerase chain reaction;*

*e) a vessel containing a template DNA comprising i) a simple or cryptically simple nucleotide sequence having a repeat motif length of 3 to 10 nucleotides and ii) nucleotide sequences flanking said simple or cryptically simple nucleotide sequence that are effective for annealing at least one pair of said primers, for assaying positive performance of the method.*

* * * * *